United States Patent [19]

Ahmad et al.

[11] Patent Number: 4,707,441
[45] Date of Patent: Nov. 17, 1987

[54] BINDING ASSAYS IN AUTOMATED APPARATUS WITH LIPOSOME COMPATIBLE SURFACTANTS

[75] Inventors: Syed I. Ahmad, Orangeburg; Eddie Hedaya, Hartsdale, both of N.Y.

[73] Assignee: Technicon Instruments Corp., Tarrytown, N.Y.

[21] Appl. No.: 638,596

[22] Filed: Aug. 6, 1984

[51] Int. Cl.$^4$ .................. G01N 33/53; G01N 33/566; G01N 35/00

[52] U.S. Cl. .......................................... 435/7; 264/4.1; 428/402.2; 436/43; 436/501; 436/829

[58] Field of Search ............... 436/821, 829, 528, 535, 436/501, 43; 435/7, 18, 810; 264/4.1; 428/402.2

[56] References Cited

U.S. PATENT DOCUMENTS 4,150,949 4/1979 Smith ........................... 436/815 X
4,483,921 11/1984 Cole ................................. 435/7

*Primary Examiner*—Sidney Marantz
*Attorney, Agent, or Firm*—Jeffrey M. Greenman

[57] ABSTRACT

Disclosed is a specific binding assay composition and method for determining a ligand in a sample. The composition comprises (a) a binding partner for the ligand; (b) a detection system which has at least two components; (c) a selectively accessible vesicle having a surface-incorporated ligand or ligand analog and a first component of the detection system therein; (d) a substance which modifies vesicle accessibility in response to binding of surface-incorporated ligand or ligand analog and the binding partner; (e) at least one additional component of the detection system which is reactive with the first component to produce a detectable response; and (f) at least one surfactant which does not modify vesicle accessibility. The composition and method are suitable for use with automated, including continuous flow-type, analyzers.

32 Claims, No Drawings

BINDING ASSAYS IN AUTOMATED APPARATUS WITH LIPOSOME COMPATIBLE SURFACTANTS

BACKGROUND OF THE INVENTION

1. Field of the Invention

This invention relates to the field of specific binding assays, particularly immunoassays, for determining substances of clinical interest. Specific binding assays are based on the specific interaction between a ligand, i.e., a bindable analyte under determination, and a binding partner therefor, i.e., receptor. Where one of the ligand and its binding partner is a hapten or antigen and the other is a corresponding antibody, the assay is known as an immunoassay.

2. Brief Description of the Prior Art

Many properties of natural cell membranes can be duplicated in simple lipid bilayer systems, referred to as liposomes. One of these properties is lysis. When a vesicular, e.g., liposome, membrane contains an externally accessible antigen it will react with corresponding antibody, causing agglutination. When the antigen-sensitized liposome reacts with corresponding antibody in the presence of complement the membrane is irreversibly damaged and can no longer function as the intact selective permeability barrier. This is immunolysis.

The extent of immunolysis has been monitored by using antigen-sensitized liposomes containing any of a wide variety of entrapped marker molecules, which are released upon immunolysis. See Hixby, et al., Proc. Nat. Acad. Sci., 64: 290–295 (1969); Kinsky, et al., Biochemistry, 8: 4149–4158 (1969); Kinsky, et al., Biochemistry, 9: 1048 (1970). See also Six, et al., Biochemistry, 13: 4050 (1974); Uemura, et al., J. Biochem, 87: 1221 (1980); and Uemura, et al., J. Immunol. Methods, 53: 221–232 (1982).

Specific binding assay systems have been proposed, using a multilayered lipid membrane vesicle which has been prepared or treated to have surface-bound ligand or ligand analog and a marker or reagent substance enclosed within the vesicle. The remaining reagents for the assay include: (1) a binding partner, e.g., antibody, for the ligand; and (2) complement to effect lysis of the vesicle upon binding of the binding partner to surface-bound ligand. Generally, see McConnell, U.S. Pat. No. 3,850,578 and McConnell, et al., U.S. Pat. No. 3,887,698 and Gregoriadis, et al., *Liposomes in Biological Systems*, John Wiley & Sons, N.Y. (1980), especially Chapter 12 entitled "Liposomes as Diagnostic Tools". Immunoassay systems have been disclosed in which the use of enzyme-encapsulating liposomes is suggested. Hsia, et al., U.S. Pat. No. 4,235,792 describes a competitive homogeneous immunoassay method which employs immunolysis of an antigen-sensitized liposome containing a marker. Enzymes are among the markers disclosed (col. 6, lines 24–28).

Numerous references in the literature have used various surfactants to achieve the chemical lysis of liposomes. This has been based on the recognized effect of such surfactant compounds on lipids and the integrity of lipid-containing membranes. Surfactants have been used to lyse liposomes, inter alia, in the development and characterization of immunoassays such as are described above. See, for example, Cole, U.S. Pat. No. 4,342,836 and the references cited therein. Another and substantially different type of liposome immunoassay is described in co-pending U.S. Ser. No. 528,496, which was filed on Sept. 1, 1983 and is assigned to the instant assignee. This also describes the use of surfactants to disrupt liposomes.

Many automated analyzers, including those of the continuous flow type, require the presence of surfactants in reagent compositions used therewith to provide appropriate hydrodynamic and optical properties to the liquids being analyzed. As such, the prior art has provided no way to accommodate these conflicting limitations of liposome specific binding assays and requirements relating to automated analysis systems.

SUMMARY OF THE INVENTION

Liposome specific binding assays offer a new approach to in vitro diagnosis. Adaptation of homogeneous immunoassays to automated clinical chemistry has become especially attractive. In particular, it is highly desirable to utilize homogeneous immunoassay methodologies on continuous flow-systems. In contrast to the prior art, this invention provides liposome-containing reagent compositions which can be utilized on automated analyzers including continuous flow systems. An especially critical component of these formulations is surfactants which are compatible with liposomes (i.e., do not lyse or otherwise modify them).

Accordingly, the present invention provides a specific binding assay composition for determining a ligand in a sample, which composition comprises (a) a binding partner for the ligand, (b) a selectively accessible vesicle having a surface incorporated ligand or ligand analogy, (c) a substance which modifies vesicle accessibility in response to binding of surface-incorporated ligand or ligand analog and the binding partner, (d) a detection system which responds to modification of vesicle accessibility to produce a detectable response, and (e) at least one surfactant which does not modify vesicle accessibility. Several embodiments of such surfactants are disclosed, each characterized in having a polyoxyethylene component.

The invention further provides a specific binding assay method, including a unique continuous flow specific binding assay method. The method comprises reacting said sample with a composition comprising: a binding partner for said ligand; a detection system having a first and second component; a selectively accessible vesicle having a surface incorporated ligand or ligand analog and, within said vesicle, a first component of said detection system which is reactive with said second component to produce a detectable response; a substance which modifies vesicle accessibility in response to binding of surface-incorporated lignad or ligand analog and the binding partner; and at least one surfactant which does not modify vesicle accessibility; and observing any detectable response so-produced. Immunoassay determinations of a broad spectrum of analytes is made possible without operator intervention and without risk of sample-to-sample carryover.

DESCRIPTION OF THE PREFERRED EMBODIMENTS

Preferred embodiments of the present invention include a specific binding assay reagent composition and method of using the test composition. Specific terms in the following description which refer only to a particular embodiment are exemplary of all of the embodiments unless otherwise indicated.

Sample fluids on which tests are performed include biological, physiological, industrial, environmental, and other types of liquids. Of particular interest are biological fluids such as serum, plasma, urine, cerebrospinal fluid, saliva, milk, broth and other culture media and supernatants as well as fractions of any of them. Other sources of sample fluid which are tested by conventional methods are contemplated as within the meaning of this term as used and can, likewise, be assayed in accordance with the invention.

The term "ligand" refers to any substance, or class of related substances, whose presence is to be qualitatively or quantitatively determined in a sample fluid, such as those just described. The present assay can be applied to the detection of ligands for which there is a specific binding partner and, conversely, to the detection of the capacity of a liquid medium to bind a ligand (usually due to the presence of a binding partner for the ligand in the sample). The ligand usually is a peptide, protein, carbohydrate, glycoprotein, steroid, or other organic molecule for which a specific binding partner exists or can be provided by immunological or synthetic means. The ligand, in functional terms, is usually selected from antigens and antibodies thereto; haptens and antibodies thereto; and hormones, vitamins, metabolites and pharmacological agents and their receptors and binding substances and normal serum constituents and disease markers.

The terms "binding partner" or "receptor" refer to any substance, or class of substances, which has a specific binding affinity for the ligand in preference to other substances. In the majority of embodiments, the present invention will incorporate specific binding assay reagents which interact with the ligand or its binding effectors in the sample in an immunochemical manner. That is, there will be an antigen-antibody or hapten-antibody relationship between reagents and/or the ligand or its binding effector in the sample. Such assays therefore are termed immunoassays and the special interaction between the ligand and its receptor, or binding partner, is immonochemical binding. However, it is well understood in the art that other binding interactions between the ligand and the binding partner serve as the basis of specific binding assays, including the binding interactions between hormones, vitamins, metabolites, and pharmacological agents, and their respective receptors and binding substances. For example, polypeptide hormone receptors as binding agents or partners are discussed in Langan, et al., (Eds.), *Ligand Assay*, Masson Publishing U.S.A. Inc., New York, pages 211 et seq (1981).

The term "selectively accessible vesicle" refers to single or multi-compartmented sacs enclosing an internal volume, having a wall composed of one or more components and forming one or more internal compartments which constitute the internal volume. One example of such a vesicle is a cell ghost, formed by opening a cellular membrane, removing the internal components of the cell and resealing the membrane. Another example is a liposome, a single or multicompartmented vesicle comprised of lipids, particularly lipid mixtures including at least one phospholipid, which form a continuous wall or bilayer lipid membrane. Additional common constituents of these lipid mixtures are cholesterol and charged long chain phospholipids. Liposomes can be prepared by any of a number of techniques. For example, multilamellar vesicles (MLVs) can be prepared by film evaporation and hydration of the lipid film. Reverse phase evaporation vesicles (REVs) may also be prepared. These are exemplary of techniques providing useful vesicles. For a general overview of liposomes and their formation, see Papahadjopoulos, et al., (Eds), Liposomes, Ann. N.Y. Acad. Sci., volume 308 (1978); Tom, et al., (Eds.), *Liposomes and Immunobiology,* Elsevier North Holland Inc., N.Y. (1980); and Gregoriadis, et al., *Liposomes in Biological Systems,* John Wiley & Sons, N.Y. (1980).

Liposomes can be made to have surface-incorporated ligand or ligand analog moieties. Such liposomes are formed using ligand-amphiphile conjugates, which usually take the form of a ligand-coupler-ampiphile molecule. Ampiphiles are substances which contain both water soluble and water insoluble regions. They are best exemplified by the lipid ampiphiles, such as the phosphatidyl ethanolamines, phosphatidyl serine, phosphatidyl inositol, sphingomyelin cerebrosides, phosphatidic acid, plasmalogens, cardiolipins and fatty acids.

Alternatively, ligands may be covalently bonded or adsorbed to the surface of preformed liposomes. When liposomes are preformed, they can have at their external surface several chemical functionalities to which antigens may be covalently linked. Appropriate reactions which may be applied to such couplings are described in Williams et al., *Methods in Immunology and Immunochemistry* Vol. 1, Academic Press, New York (1967). In some cases, antigens may be adsorbed to the liposome surface, as was shown by Uemura and Kinsky, Biochemistry, 11: 4085–4094 (1972).

The composition of the invention further includes a substance which modifies vesicle accessibility in response to binding of surface-incorporated ligand or ligand analog and the binding partner. The principal example of this substance is a group of compounds collectively referred to as complement. For a general overview of complement and its effects, see Rapp, et al., *Molecular Basis of Complement Action,* Appleton-Century-Crofts (1970). Also, the role of complement is discussed in many of the references addressing other liposome immunoassays which have been cited above.

The composition can use any of the variety of detection systems which have been recognized for such purposes, including those described in the references cited above. Additionally, the compositions can provide a detection system such as that described in co-pending Ser. No. 528,496 which was filed on Sept. 1, 1983 and is assigned to the instant assignee.

In accordance with the present invention, the composition further includes at least one surfactant which does not modify vesicle accessibility or interfere with the immunological interactions which form the basis for the specific binding assay. Such surfactants are included in the overall immunoassay reagent composition in a concentration range of from about 0.1 to about 1.0 percent.

One embodiment of the invention includes polyoxyethylene polymers having at least about 23 ethylene oxide monomer units. These can have, in addition, hydrophobic groups of from about $C_8$–$C_{17}$, including aromatic and aliphatic constituents. Examples of this embodiment include: polyoxyethylene lauryl ether having at least 23 ethylene oxide units (Brij-35, ICI United States, Inc., Wilmington, DE); nonyl phenoxy polyethoxyethanol having at least 30 ethylene oxide monomer units (Igepal CO-880, GAF Corp., N.Y., NY); and octyl phenoxy polyethoxy ethanol having at least 30 ethylene oxide monomer units (TRITON X-305, Rohm & Haas, Philadelphia PA).

Another embodiment of the invention includes surfactants which have the formula:

$$HO(C_2H_4O)_a(C_3H_6O)_b(C_2H_4O)_cO$$

where b is at least 15 and a plus c is from about 11 to about 73. Preferred are those in which a plus c is selected from the group of 11, 18, 34, 41, 46, 49, 51 and 73. Such surfactants are available under the PLURONIC trademark from BASF-Wyandotte Corp., Parsippany, NJ.

A third embodiment of the invention includes surfactants which have the formula:

$$[H(C_2H_4O)_a(C_3H_6O)_b]_2NCH_2CH_2N[(C_3H_6O)_b(C_2H_4O)_c]_2$$

where b is at least 5, preferably from about 5 to 15, and a plus c is from about 30 to 113. Preferred among these are compounds where a plus c is selected from the group of 30, 50, 68, 75, 95 and 113. Such surfactants are available under the TETRONIC trademark from BASF-Wyandotte Corp., supra.

The invention further provides a specific binding assay method. The method comprises reacting said sample with a composition comprising: a binding partner for said ligand; a detection system having a first and second component; a selectively accessible vesicle having a surface incorporated ligand or ligand analog and, within said vesicle, a first component of said detection system which is reactive with said second component to produce a detectable response; a substance which modifies vesicle accessibility in response to binding of surface-incorporated ligand or ligand analog and the binding partner; and at least one surfactant which does not modify vesicle accessibility; and observing any detectable response so-produced.

In a preferred embodiment the sample is reacted with a first composition comprising (i) a binding partner for the ligand, (ii) a second component of a detection system having a first and second component and (iii) a first surfactant independently selected from those of the invention. The resulting reaction mixture is reacted with a second composition comprising (iv) a selectively accessible vesicle having a surface incorporated with ligand or ligand analog and, within the vesicle, a first component of the detection system which is reactive with the second component to produce a detectable response, (v) a substance which modifies vesicle accessibility in response to binding of surface-incorporated ligand or ligand analog and the binding partner, and (vi) a second surfactant independently selected from those of the invention. Any resulting detectable response so-produced is then detected.

In a particularly preferred embodiment, the sample is reacted with a first composition comprising (i) antibody to the ligand, (ii) components of the detection system comprising an enzyme substrate and a substance which is detectably altered by the interaction of the substrate with an enzyme therefor and (iii) a surfactant as described to form a reaction mixture. Then, the resulting reaction mixture is reacted with a second composition comprising (iv) a liposome having a surface incorporated with ligand or ligand analog and, within the liposome, an enzyme which is reactive with the substrate to so alter the detectably alterable substance, (v) complement and (vi) a surfactant as described. The detectable response is preferably colorimetric or luminescent.

As discussed above, the composition of the invention is particularly useful in continuous flow systems. One such system in which such compositions are of particular interest is described in co-pending Ser. No. 441,881 which was filed on Nov. 15, 1982 and assigned to the instant assignee. By way of a specific example, a specific binding assay in accordance with this invention can be performed on such a continuous flow system for detecting a ligand in selected liquid segments of a stream of an alternating sequence of gas and liquid segments flowing in a single conduit having sequential first, second and third sections. In the method of the invention, as performed in such a system, a first liquid segment of a sample suspected to contain the ligand and a first reagent comprising (i) a binding partner for the ligand, (ii) a second component of a detection system having a first and second component, and (iii) a surfactant selected from those previously described is introduced into the conduit. Then, a first air segment which is occlusive in the first conduit section is introduced. Then, a second liquid segment of a second reagent comprising (iv) a selectively accessible vesicle having a surface incorporated with ligand or ligand analog and, within the vesicle, a first component of a detection system which is reactive with the second component to produce a detectable response, (v) a substance which modifies vesicle accessibility in response to binding of surface-incorporated ligand or ligand analog and the binding partner, and (vi) a surfactant selected from those previously described is introduced. A second air segment which is occlusive in the first conduit section is then introduced. The segments are maintained separate while in the first conduit section and the segments which had been maintained separate in the first conduit section are passed into a second conduit section having a diameter sufficiently greater than that of the first conduit section to render the first gas segment non-occlusive in the second section. The first and second liquid segments are combined and the first and second gas segments are coalesced in the second conduit section. The combined liquid segment is maintained separate from other liquid segments by occluding the second and third conduit sections with the coalesced gas segment and is completely mixed in the third conduit section. The completely mixed combined liquid segment is then analyzed for a detectable response while it is passing through the third conduit section.

The following working examples describe experiments which were performed in developing the present invention. Standard commercially available reagent grade chemicals were used whenever possible.

EXAMPLE I

Dilantin-Liposome Compatible Surfactants

In the experiments reported by this example, immunoassay reagent compositions comprising a dilantin-liposome containing B-galactosidase, complement, antibody to dilantin, O-nitrophenyl B-D galactoside (chromogen) and various surfactants were evaluated to determine the effect of each surfactant on the chemical or immunolysis of the liposome. No sample or free dilantin was included in this evaluation of the reagent so that maximum immunolysis could be observed.

Liposome Preparation

Liposomes containing dilantin and B-galactosidase enzyme were prepared as follows. A mixture was prepared to contain 22 milligrams (mg) egg lecithin (Sigma Chemical Co., St. Louis, MO), 8.70 mg cholesterol (Sigma, supra), 0.65 mg dl-atocopherol (Sigma, supra), and 2.76 mg of a dilantin-ampiphile conjugate in 100 ml chloroform. Such a dilantin conjugate can be prepared by the procedure described in Haga, et al, *Biochem Biophys. Res Comm.* 90:187-192 (1980). The mixture so prepared as introduced into a 500 ml flask of a rotary evaporator. The flask was rotated therein and evaporation of the chloroform was conducted under vacuum by water aspiration at 40° centigrade (C.) until a dry film was observed on the inside surface of the flask. Thereafter, this film was further dried for one hour under vacuum at 0.25 mm mercury. The film was hydrated with 7 ml of TRIS buffer stock solution, described below, containing 7.8 mg B-galactosidase (Sigma, supra) overnight at 4° C. with stirring. The liposomes so-prepared were separated from components of the mixture which had not formed liposomes by using a Model L8-55 Beckman ultracentrifuge at 32,000 rpm at 8° C. for 25 minutes.

Other Preparations

The TRIS buffer stock solution (pH 7.5) was prepared by combining 60.5 gram/liter (g/l) tris hydroxymethyl aminomethane with 8.7 g/l sodium chloride and 1 g/l sodium azide.

Antidilantin antibody solution was prepared from commercially available anti-dilantin rabbit antiserum (Cappel Laboratories, Cockrahnville, PA). A 900 ul volume of TRIS buffer stock solution was added to a vial containing 100 ul of the Cappel antiserum to make a 1:10 (v/v) stock antibody solution.

Complement solution was prepared by reconstituting 1 g lyophilized guinea pig serum (Pel Freez, Rogers, AK) with 3 ml TRIS buffer stock solution.

The surfactant solutions selected from comparison were each prepared by dissolving 1 gm of surfactant in 100 ml of TRIS buffer stock solution to make a 1% (w/v) solution. The various surfactants were Tritons (Rohm and Haas, Philadelphia, PA), Igepals (GAF Corp, New York, NY), PEG-4000 (Union Carbide, New York, NY), Brij-35 (ICI America Inc., Wilmington, DE), Pluronics (BASF-Wyandotte Corp., supra) and Tetronics (BASF-Wyandotte Corp., supra). They are set forth in Table I, as are the number of ethylene oxide (EtO) molecules in each.

Reagent Preparations

Reagent $R_1$ was made by combining 100 ul of complement solution, 100 ul anti-dilantin antibody solution, 100 ul nitrophenol B-D-galactoside as substrate and 50 ul TRIS buffer stock solution.

Reagent $R_2$ was made by combining 5 ul of the liposome preparation, 255 ul TRIS buffer stock solution and 70 ul of a selected one of the surfactants for each $R_1$ preparation. The final surfactant concentration was 0.1% (v/v) in each instance.

Assay Procedure

A 350 ul volume of each of Reagent $R_1$ and $R_2$ was mixed together and pipetted into the flow-through cuvette of a Model 260 Gilford Spectrophotometer which was used in accordance with the manufacturer's directions (Gilford Instruments Co., Oberlin, OH). The rate of the reaction was recorded at 405 nm by dividing the difference in optical density observed over a given time. The first experiment was performed on mixtures in which surfactants were present (S+) and dilantin antibody had been omitted (AB−). In the second set of experiments, surfactant (S+) and antibody (AB+) were both present. The ratio of the rates of hydrolysis of B-galactoside substrate, with and without antibody (AB+/AB−), were as set forth in Table I. This shows certain surfactants lyse liposomes even in the absence of antibody and that the surfactants evaluated did not interfere with immunolysis.

In the next two experiments, surfactant in reagent $R_2$ was replaced by an equal volume of TRIS buffer stock solution. Antibody was included in the first and excluded from the second of these experiments. This was done to show that immunolysis had occurred in the absence of surfactant and to provide a blank. From the first experiment above and the blank, the ratio of B-galactoside hydrolysis rates were obtained, with and without surfactant (S+/S−), and are also set forth in Table I.

TABLE I

| Surfactant | EtO | AB+/AB− | S+/S− |
|---|---|---|---|
| TRIS buffer | — | 2.5 | 1.0 |
| Igepal CO-630 | 10–11 | — | 2.6 |
| Igepal CO-710 | 20 | — | 3.0 |
| Igepal CO-880 | 30 | 2.5 | 1.0 |
| Triton X-100 | 9–10 | — | 4.0 |
| Triton X-102 | 12–13 | — | 4.0 |
| Triton X-165 | 16 | — | 4.0 |
| Brij-35 | 23 | 2.5 | 1.0 |
| Triton X-305 | 30 | 2.5 | 1.0 |
| PEG (4000) | 90 | 2.5 | 1.0 |
| Pluronic L-43 | 11 | 2.5 | 1.0 |
| Pluronic L-44 | 18 | 2.5 | 1.0 |
| Pluronic L-62 | 9 | — | 3.7 |
| Pluronic L-63 | 17 | 2.5 | 1.0 |
| Pluronic L-64 | 26 | 2.5 | 1.0 |
| Pluronic P-75 | 46 | 2.5 | 1.0 |
| Pluronic P-84 | 34 | 2.5 | 1.0 |
| Pluronic P-85 | 51 | 2.5 | 1.0 |
| Pluronic P-94 | 41 | 2.5 | 1.0 |
| Pluronic P-104 | 49 | 2.5 | 1.0 |
| Pluronic P-105 | 73 | 2.5 | 1.0 |
| Tetronic 504 | 30 | 2.5 | 1.0 |
| Tetronic 704 | 50 | 2.5 | 1.0 |
| Tetronic 904 | 75 | 2.5 | 1.0 |
| Tetronic 1104 | 95 | 2.5 | 1.0 |
| Tetronic 1304 | 113 | 2.5 | 1.0 |
| Tetronic 1504 | 46 | 2.5 | 1.0 |

Conclusions

The Igepal and Triton surfactants, respectively, nonyl and octyl phenols with EtO monomer units fewer than 23 were found to lyse liposomes as shown by the S+/S− ratios and, thus, effectively prevented any determination based on immunolysis. However, the Brij-35 surfactant, with 23 EtO monomer units, Igepal, Triton and PEG 4000 surfactants with 30 or more EtO monomer units did not cause lysis or interfere with the immunological reaction. Also, Tetronic surfactants with 30 or more EtO monomer units did not lyse the liposomes or interfere with the immunological reaction.

Even more surprisingly, Pluronic surfactants with as few as 11 EtO monomer units did not lyse the liposomes or interfere with the immunological reaction.

EXAMPLE II

Phenobarbital Liposome Compatible Surfactant

The experiments reported in this example were performed to determine the effect of various surfactants on liposomes carrying phenobarbital on their surface when used in immunoassay compositions on an automated random access batch analyzer. No sample or free phenobarbital was included in this evaluation so that maximum immunolysis could be observed.

The composition of reagents $R_1$ and $R_2$ was as follows:

| Reagent $R_1$ | |
|---|---|
| 1. Substrate | 235 ul |
| 2. Antibody (1:100) | 25 ul |
| 3. Complement (1:2) | 40 ul |
| 4. Surfactant (1%) | 40 ul |
| 5. TRIS Buffer | 35 ul |
| Reagents $R_2$ | |
| 1. Liposome (1:20) | 15 ul |
| 2. TRIS Buffer | 30 ul |
| 3. Surfactant (1%) | 5 ul |

The liposomes were made as described in Example I, except that a phenobarbital conjugate was used. All of the other stock solution preparations were as described in Example I, except that anti-phenobarbital rabbit antiserum from Cappel Laboratories, supra, was used.

The determinations were performed on an RA-1000 analytical system according to the manufacturer's protocol (Technicon Instruments Corporation, Tarrytown, NY).

The same comparisons were made as in Example I to determine the effect of various surfactants. The results are shown in Table II.

TABLE II

EFFECT OF SURFACTANTS ON PHENOBARBITOL LIPOSOME

| Surfactant | $AB^+/AB^-$ | $S^+/S^-$ |
|---|---|---|
| TRIS buffer | 6.8 | 1 |
| Igepal CO-630 | — | 6.8 |
| Igepal CO-710 | — | 6.8 |
| Igepal CO-880 | 6.5 | 1 |
| Triton X-100 | — | 6.8 |
| Triton X-102 | — | 6.8 |
| Triton X-305 | 6.5 | 1 |
| Brij-35 | 6.5 | 1 |
| Pluronic L-43 | 6.8 | 1 |
| Pluronic P-84 | 6.8 | 1 |
| Pluronic P-85 | 6.8 | 1 |
| Pluronic P-104 | 6.8 | 1 |
| Pluronic P-105 | 6.8 | 1 |
| Tetronic 504 | 6.4 | 1 |
| Tetronic 704 | 6.4 | 1 |
| Tetronic 904 | 6.4 | 1 |
| Tetronic 1104 | 6.4 | 1 |
| Tetronic 1304 | 6.4 | 1 |
| Tetronic 1504 | 6.4 | 1 |

Conclusions

Triton and Igepal surfactants with 10–20 EtO monomer units were found to lyse liposomes ($S^+/S^- = 6.5-6.8$) and, thus, effectively prevented any determination based on immunolysis. However, Brij-35, Triton X-305 and Igepal CO-880 did not lyse the liposomes. Likewise, Tetronic surfactants with 30 or more EtO monomers and Pluronic surfactants having 11 to 73 EtO monomers do not lyse the liposomes ($S^+/S^- = 1$).

EXAMPLE III

Phenobarbital Immunoassay Using Pluronic 105 Surfactant

The experiments reported by this example demonstrate the use of an immunoassay composition in accordance with the invention for determination of phenobarbital in an automated clinical analyzer.

Reagents $R_1$ and $R_2$ used here were exactly as those described in Example II, using Pluronic P-105 as surfactant, and the experiments were performed on an RA-1000 system according to the protocol provided by the manufacturer (Technicon, supra).

Dose/response relationships were observed using phenobarbital liposomes with and without surfactant. Emit controls (Syva Company, Palo Alto, CA) having phenobarbital concentrations of 0, 5, 10, 20, 40 and 80 ug/ml were used as "ligand-containing sample" to generate data demonostrating this dose/response relationship. The effect of the presence and absence of Pluronic P-105 surfactant on lysis of liposome is given in Table III.

TABLE III

EFFECT OF PLURONIC 105 ON PHENOBARBITAL DETERMINATION

| Phenobarbital | % Lysis | |
|---|---|---|
| (ug/ml) | Without | With |
| 0 | 100 | 100 |
| 5 | 85 | 84 |
| 10 | 69 | 66 |
| 20 | 52 | 50 |
| 40 | 19 | 19 |
| 80 | 6 | 6 |

As can be seen from these data, the Pluronic 105 surfactant had no effect on the immunoassay reactions or resulting accuracy of the reported ligand concentration at any point over the entire range covered.

Then, a comparison study in which phenobarbital was determined in human serum samples was carried out in the presence and absence of Pluronic 105 surfactant on the RA-1000 system as described above. The correlation coefficient was found to be 0.986 with a slope of 0.97.

Thus, it has been demonstrated that the present invention provides an immunoassay reagent and method which is dose-responsive and provides results which correlate well with the same method in the absence of surfactant.

EXAMPLE IV

Phenobarbital Immunoassay Using Tetronic 704 Surfactant

The experiments reported by this example demonstrate the use of an immunoassay composition in accordance with the invention for determination of phenobarbital in an automated clinical analyzer.

Reagents $R_1$ and $R_2$ used here were exactly as those described in Example II, using Tetronic 704 as surfactant, and the experiments were performed on an RA-1000 system according to the protocol provided by the manufacturer (Technicon, supra).

Dose/response relationships were observed using phenobarbital liposomes with and without surfactant. Emit controls (Syva Company, Palo Alto, CA) having phenobarbital concentrations of 0, 5, 10, 20, 40 and 80 ug/ml were used as "ligand/containing sample" to generate data demonstrating this dose/response relationship. The effect of the presence and absence of Tetronic 704 surfactant on lysis of liposome is given in Table IV.

TABLE IV

EFFECT OF TETRONIC 704 ON PHENOBARBITAL DETERMINATION

| Phenobarbital | % Lysis | |
|---|---|---|
| (ug/ml) | Without | With |
| 0 | 100 | 100 |

TABLE IV-continued
EFFECT OF TETRONIC 704 ON PHENOBARBITAL DETERMINATION

| Phenobarbital | % Lysis | |
| --- | --- | --- |
| (ug/ml) | Without | With |
| 5 | 90 | 90 |
| 10 | 72 | 70 |
| 20 | 55 | 52 |
| 40 | 22 | 21 |
| 80 | 8 | 7 |

As can be seen from these data, the Tetronic 704 surfactant had no effect on the immunoassay reactions or resulting accuracy of the reported ligand concentration at any point over the entire range covered.

Then, a comparison study in which phenobarbital was determined in human serum samples was carried out in the presence and absence of Tetronic 704 surfactant on the RA-1000 system as described above. The correlation coefficient was found to be 0.960 with a slope of 0.96.

Thus, it has been demonstrated that the present invention provides an immunoassay reagent and method which is dose-responsive and provides results which correlate well with the same method in the absence of surfactant.

What is claimed is:

1. A composition suitable for use in an automated analysis system for determining an analyte ligand in a sample, which composition comprises:
   (a) a binding partner for said analyte ligand;
   (b) a detection system which has at least two components;
   (c) a vesicle, which is selectively repurturable or permeable by an external medium surrounding the vesicle, having a vesicle surface-incorporated analyte ligand or analyte ligand analog, and a first component of the detection system contained within the vesicle;
   (d) a substance which modifies vesicle rupturability or permeability of the external medium surrounding the vesicle in response to binding of the surface-incorporated analyte ligand or analyte ligand analog and the binding partner;
   (e) at least one additional component of the detection system which is reactive with the first component of the detection system to produce a detectable response; and
   (f) at least one surfactant which does not modify vesicle rupturability or permeability by the external medium surrounding the vesicle.

2. The composition of claim 1 wherein the vesicle comprises a lipid membrane.

3. The composition of claim 2 wherein the lipid membrane comprises a phospholipid.

4. The composition of claim 2 wherein the lipid membrane incorporates a sterol.

5. The composition of claim 2 wherein the lipid membrane includes an ampiphile to which the analyte ligand or analyte ligand analog is bound.

6. The composition of claim 1 wherein the surfactant is a polyoxyethylene polymer having at least about 23 ethylene oxide monomer units.

7. The composition of claim 6 wherein the surfactant further comprises a $C_8$–$C_{17}$ hydrophobic group.

8. The composition of claim 7 wherein the surfactant is a polyoxyethylene lauryl ether.

9. The composition of claim 7 wherein the surfactant is a nonyl phenoxy polyethoxyethanol having at least 30 ethylene oxide monomer units.

10. The composition of claim 7 wherein surfactant is an octyl phenoxy polyethoxy ethanol having at least 30 ethylene oxide monomer units.

11. The composition of claim 1 wherein the surfactant has the formula:

$$HO(C_2H_4O)_a(C_3H_6O)_b(C_2H_4O)_cH$$

where b is at least 15 and a plus c is from about 11 to 73.

12. The composition of claim 11 wherein a plus c is selected from 11, 18, 34, 41, 46, 49, 51 and 73.

13. The composition of claim 1 wherein the surfactant has the formula:

$$[H(C_2H_4O)_a(C_3H_6O)_b]_2NCH_2CH_2N[(C_3H_6O)_b(C_2H_4O)_cH]_2$$

where b is at least 5 and a plus c is from about 30 to 113.

14. The composition of claim 13 wherein a plus c is selected from 50 and 75.

15. A composition suitable for use in an automated analysis system for determining the presence of an analyte ligand in a test sample, which composition comprises:
   (a) an antibody to said analyte ligand;
   (b) a liposome containing B-galactosidase, the liposome having analyte ligand or analyte ligand analog bound to its surface;
   (c) complement;
   (d) a substrate capable of interacting with B-galactosidase;
   (e) a substance which provides a detectable response upon the interaction of the B-galactosidase and the substrate; and
   (f) at least one surfactant which does not modify liposome rupturability or permeability by the external medium surrounding the liposome.

16. The composition of claim 15 wherein the surfactant is a polyoxyethylene polymer having at least about 23 ethylene oxide monomer units.

17. The composition of claim 16 wherein the surfactant futher comprises a $C_8$–$C_{17}$ hydrophilic group.

18. The composition of claim 17 wherein the surfactant is a polyoxyethylene lauryl ether.

19. The composition of claim 17 wherein the surfactant is a nonyl phenoxy polyethoxyethanol having at least 30 ethylene oxide monomer units.

20. The composition of claim 17 wherein the surfactant is an octyl phenoxy polyethoxy ethanol having at least 30 ethylene oxide monomer units.

21. The composition of claim 15 wherein the surfactant has the formula:

$$HO(C_2H_4O)_a(C_3H_6O)_b(C_2H_4O)_cH$$

where b is at least 15 and a plus c is from about 11 to 73.

22. The composition of claim 21 wherein a plus c is selected from 11, 18, 34, 41, 46, 49, 51 and 73.

23. The composition of claim 15 wherein the surfactant has the formula:

$$[H(C_2H_4O)_a(C_3H_6O)_b]_2NCH_2CH_2N[(C_3H_6O)_b(C_2H_4O)_cH]_2$$

where b is at least 5 and a plus c is from about 30 to 113.

24. The composition of claim 23 wherein a plus c is selected from 50 and 75.

25. A specific binding assay method for use in an automated analysis system for determining the presence of an analyte ligand in a sample, the method comprising the steps of:
   contacting the test sample with a composition comprising a binding partner for the analyte ligand; a detection system comprising a first compound and a second compound; a vesicle containing the first compound of said detection system and having incorporated with its surface analyte ligand or analyte ligand analog; a substance which modifies the rupturability or permeability of the medium external to the vesicle; and at least one surfactant which does not modify vesicle rupturability or permeability by the medium external to the vesicle; and observing any detectible response.

26. A specific binding assay method for use in an automated apparatus for determining the presence of an analyte ligand in a test sample, the method comprising:
   (a) contacting the sample with a composition comprising a binding partner for the analyte ligand the second component of a detection system having a first and a second component, and at least one surfactant;
   (b) contacting the mixture of step (a), above, with a second composition comprising a vesicle which is selectively rupturable or permeable by a medium external to the vesicle, which vesicle has incorporated with its surface analyte ligand or analyte ligand analog; the vesicle containing the first component of the detection system; a substance which modifies vesicle rupturability or permeability by the medium surrounding the vesicle in response to binding of surface-incorporated analyte ligand or analyte ligand analog and the binding partner; and at least one surfactant; and observing any detectable response with the proviso that the at least one surfactant of (a) and (b) does not modify vesicle rupturability or permeability by the medium surrounding the vesicle.

27. The specific binding assay method of claim 26 wherein:
   (a) comprises reacting the sample with a first composition comprising (i) antibody to said ligand, (ii) components of said detection system comprising an enzyme substrate and a substance which is detectably altered by the interaction of the substrate with an enzyme therefor and (iii) at least one surfactant which does not modify vesicle rupturability or permeability;
   (b) comprises reacting the reaction mixture of (a) with a second composition comprising (iv) a liposome having a surface incorporated with ligand or ligand analog and, within said liposome, an enzyme which is reactive with said substrate to so alter said detectably alterable substance, (v) complement and (vi) at least one surfactant which does not modify vesicle rupturability or permeability.

28. A method for performing specific binding assay in a fluid system of controlled hydrodynamic characteristics which method comprises:
   reacting in said fluid system a sample with a composition comprising: a binding partner for said ligand; a detection system having a first and second component; a selectively accessible vesicle having a surface-incorporated ligand or ligand analog and, within said vesicle, a first component of said detection system which is reactive with said second component to produce a detectable response; a substance which modifies vesicle rupturability or permeability in response to binding of surface-incorporated ligand or ligand analog and the binding partner; and at least one surfactant which does not modify vesicle rupturability or permeability and is compatible with hydrodynamic requirements of the fluid system; and observing any detectable response so-produced.

29. A specific binding assay method for detecting a ligand in selected liquid segments of a stream of an alternating sequence of gas and liquid segments flowing in a single conduit having a single inlet and sequential first, second and third sections, which method comprises:
   (a) introducing into said single inlet a first liquid segment of a sample suspected to contain said ligand and a first reagent comprising (i) a binding partner for said ligand, (ii) a second component of a detection system having a first and second component and (iii) at least one surfactant which does not modify vesicle accessibility;
   (b) introducing into said single inlet a first air segment which is occlusive in said single inlet and said first conduit section;
   (c) introducing into said single inlet a second liquid segment of a second reagent comprising (iv) a selectively accessible vesicle having a surface incorporated with ligand or ligand analog and, within said vesicle, a first component of a detection system which is reactive with said second component to produce a detectable response, (v) a substance which modifies vesicle rupturability or permeability accessibility in response to binding of surface incorporated ligand or ligand analog and the binding partner, and (vi) at least one surfactant which does not modify vesicle rupturability or permeability;
   (d) introducing into said single inlet a second air segment which is occlusive in said inlet and said first conduit section;
   (e) maintaining said segments separate while in said probe and first conduit sections;
   (f) passing said segments which had been maintained separate in said first conduit section having a diameter sufficiently greater than that of said first conduit section to render said first gas segment non-occlusive in said second section;
   (g) combining said first and second liquid segments in said second conduit section;
   (h) coalescing said first and second gas segments in said second conduit section;
   (i) maintaining said combined liquid segment separate from other liquid segments by occluding said second and third conduit sections with said coalesced gas segment;
   (j) completely mixing said combined liquid segments in said third conduit section;
   (k) analyzing said completely mixed combined liquid segment for said detectable response while it is passing through said third conduit section.

30. The method of claim 29 wherein each of said surfactants is independently selected from a polyoxyethylene polymer having at least about 23 ethylene oxide monomer units.

31. The method of claim 29 wherein each of said surfactants is independently selected from those having the formula:

$$HO(C_2H_4O)_a(C_3H_6O)_b(C_2H_4O)_cH$$

where b is at least 15 and a plus c is from about 11 to 73.

32. The method of claim 29 wherein each of said surfactants is independently selected from those having the formula:

$$[H(C_2H_4O)_a(C_3H_6O)_b]_2N\\CH_2CH_2N[(C_3H_6O)_b(C_2H_4O)_cH]_2$$

where b is at least 5 and a plus c is from about 30 to 113.

* * * * *